United States Patent [19]
Schaeffer et al.

[11] B 3,987,106
[45] Oct. 19, 1976

[54] MANUFACTURE OF ACETALDEHYDE
[75] Inventors: William D. Schaeffer, Pomona; Kenneth L. Olivier, Placentia, both of Calif.
[73] Assignee: Union Oil Company of California, Brea, Calif.
[22] Filed: Dec. 16, 1971
[21] Appl. No.: 208,916
[44] Published under the second Trial Voluntary Protest Program on January 13, 1976 as document No. B 208,916.

Related U.S. Application Data
[63] Continuation of Ser. No. 572,899, Aug. 17, 1955, abandoned.

[52] U.S. Cl. .............................................. 260/601 R
[51] Int. Cl.² ............................................ C07C 47/06
[58] Field of Search ................................ 260/601 R

[56] References Cited
UNITED STATES PATENTS
3,119,874  1/1964  Paszthory et al. .................. 260/597

OTHER PUBLICATIONS
Bobtelsky et al., J. Am. Chem. Soc. vol. 64, pp. 1462–1468 (1942).
Jones et al., J. Chem. Soc. pp. 4757–4761 (1961).
Marette et al., "Chem. Abst." 48, p. 4941g (1954).
Bhargova et al., "Chem. Abst." 63, p. 11291b (1965).

Primary Examiner—Paul M. Coughlan, Jr.
Assistant Examiner—W. B. Springer
Attorney, Agent, or Firm—Michael H. Laird; Dean Sandford; Richard C. Hartman

[57] ABSTRACT
The destructive oxidation of oxalic acid is catalyzed by a vanadium compound in liquid phase oxidation. The oxalic acid is contacted with oxygen in the presence of a vanadium compound in aqueous solution and the oxidation proceeds selectively without any appreciable oxidation of other components of the reaction medium such as acetaldehyde and ethylene. The oxidation is performed at temperatures between 30° and 300°C. and atmospheric or superatmospheric pressure.

5 Claims, No Drawings

MANUFACTURE OF ACETALDEHYDE

This application is a continuation of Ser. No. 572,899 filed Aug. 17, 1955, now abandoned.

DESCRIPTION OF THE INVENTION

This invention relates to a process for oxidizing olefins to carbonyl compounds and in a specific embodiment relates to the oxidation of ethylene to acetaldehyde and acetic acid.

It is known that a hydrocarbon olefin such as ethylene can be continuously oxidized by contacting the olefin with water or water vapor in the presence of a platinum group metal salt. This reaction can be performed in the vapor phase by impregnating the catalyst on a suitable support or in the liquid phase by employing an aqueous solution of soluble salts of the platinum group metal. During the oxidation, a stoichiometric quantity of the platinum group ions are reduced to metal and, to provide a continuous process, a method for oxidizing the platinum group metal must be provided. Recently published literature has disclosed such a method by suggesting the use of a redox agent that can be maintained in an oxidized state with molecular oxygen and, when in its oxidized state, can oxidize the platinum group metal. While a great many agents have been suggested for this purpose including salts of almost the entire series of transition metals, cupric salts appear unique in their redox activity and are used exclusively for this purpose.

In the presence of a cupric salt the platinum group metal is oxidized to its higher valence state for reaction with a further quantity of olefin. After the oxidizing inventory of the solution is depleted, i.e., when copper is present as cuprous ions and the platinum group metal is in its reduced state, the catalyst, either on a fixed support or suspended in the aqueous medium, is regenerated. Two techniques can be used for oxidation of the catalyst; in one technique relatively pure oxygen is employed and is introduced simultaneously into the reactor with the olefin. According to this procedure, the oxidation proceeds continuously in a single reactor, the oxygen oxidizing the cuprous ions to cupric and the latter oxidizing the reduced platinum group metal which, ultimately, oxidizes the olefin. According to an alternative arrangement, air or other mixtures of oxygen with inert gases is used in a separate regeneration for oxidation of the catalyst solid or solution. In this embodiment, after the oxidizing inventory of the system has been depleted by reaction with the olefin, the contact with the olefin is discontinued and the oxygen is thereafter introduced into contact with the reduced system. When employed in the liquid phase system, this method is conveniently practiced by circulating a slurry or solution of the catalyst through alternate reaction or regeneration zones. When practiced on a vapor phase oxidation employing a solid supported catalyst, the method is practiced by alternately introducing the olefin and the oxygen-containing gas into contact with the solid in the reactor.

During the aforedescribed oxidation, an unavoidable oxidation of the olefin to oxalic acid also occurs. While this side reaction does not cause an appreciable loss of the olefin feed, it is particularly troublesome since cupric oxalate is highly insoluble. Therefore, the conversion of the olefin to oxalic acid ultimately results in precipitation of the copper redox agent from the system, either as an inactive deposit on the solid catalyst or as an insoluble and inert precipitate in the liquid phase system. The existence of this problem has been recognized in commercial plants; e.g., see *Canadian Chemical Processing*, July 1963, pages 63–66. All proposed solutions for this problem have required a separate regeneration of all or a portion of the catalyst; see U.S. Pat. No. 3,076,032. The proposed methods are costly and encumber an otherwise elegant oxidation process.

It is an object of this invention to provide for the destructive oxidation of the oxalic acid byproduct of said oxidation without use of separate catalyst treatments.

It is also an object of this invention to provide a catalyst and use thereof for the destructive and selective oxidation of oxalic acid and oxalates in the presence of easily oxidizable substrates such as acetaldehyde and olefins.

It is a further object of this invention to provide for the use of the aforementioned catalyst directly in the olefin oxidation process in the presence of the platinum group metal and copper salt catalyst.

Other and related objects will be apparent from the following description of the invention.

The aforestated object of selective oxidation of oxalic acid is achieved by the process of this invention which comprises contacting at a temperature from 30° to 300°C. a liquid mixture of water, acetaldehyde and oxalic acid with oxygen and catalytic amounts of a vanadium compound soluble in said liquid mixture.

We have now found that oxalic acid can be destructively oxidized during the aforedescribed olefin oxidation and the precipitation of the copper redox agent prevented by the incorporation of a soluble vanadium compound in the reaction medium or by impregnation of the solid catalyst support with a suitable vanadium compound. In general, between about .01 and about 1.0 weight percent based on the catalyst solution or between about 0.05 and about 5.0 weight percent based on the solid catalyst composition of a vanadium compound can be used. Suitable vanadium compounds include, e.g., vanadium dichloride, vanadium tetrachloride, vanadium tetroxide, vanadium dibromide, vanadium tetrabromide, vanadium trichloride, vanadyl bromide, vanadyl chloride, vanadyl sulfate, vanadyl nitrate, as well as various vanadate salts such as sodium vanadate, potassium vanadate, etc.

We are aware that compounds of many multivalent metals, including vanadium have been suggested as redox agents in the aforementioned olefin oxidation. To illustrate, compounds of mercury, cerium, thallium, tin, lead, titanium, vanadium, antimony, chromium, molybdenum, uranium, manganese, iron, cobalt and nickel have been suggested for use as redox agents; see Patent 3,119,874. None of the compounds of the preceding metals, however, will catalyze the destructive oxidation of oxalic acid or oxalates except the compounds of vanadium. In fact, a number of the preceding metals are unstable in the aqueous and acidic reaction medium used in the oxidation; e.g., titanium and antimony form insoluble oxides, thallium precipitates as the insoluble thallous halide and mercury and lead are quickly reduced to an inert lower valency.

Of the preceding metals, vanadium alone catalyzes the oxidation of oxalic acid. This catalytic activity is independent of any redox activity that the metal exhibits as will be illustrated in the exemplified portion of this description of the invention. The uniqueness of this catalytic activity of vanadium compounds, the recognition of the oxalate problem by prior investigators and their failure to discover the catalytic activity of vanadium evidence the unexpected nature of our discovery.

The oxidation process is conducted at relatively mild conditions, temperatures between about 30° and about 300°C., preferably between about 100° and 250°C., and pressures from atmospheric to about 750 atmospheres, preferably between about 10 and about 300 atmospheres, sufficient to maintain liquid phase conditions in the liquid phase contacting scheme. Suitably lower pressures are employed for the vapor phase operation, generally pressures from about atmospheric to about 5 atmospheres being preferred.

As previously mentioned, the catalytic component of the system comprises a platinum group metal such as platinum, rhodium, palladium, ruthenium, iridium and osmium. Of these, palladium is preferred because of its demonstrated greater activity. In general, the catalyst solution and/or catalyst solid composite should comprise between about 0.01 and about 5.0 weight percent of a suitable palladium compound.

Although a host of redox agents have been suggested by prior investigators, cupric compounds are the commonly used redox agents because of their high activity and solubility. The cupric compound is employed as a soluble salt in the aqueous reaction medium or is impregnated as a salt on the solid support for the vapor phase contacting technique. In general, any water soluble cupric salt can be employed for this purpose including the halides, e.g., chlorides, bromides, sulfates; nitrates; etc. In the liquid phase contacting technique, the concentration of the cupric salt is limited only by its solubility and concentrations from about 1 to about 20 weight percent of the solution are used. In vapor phase contacting, preferably the multivalent cupric salt deposit comprises between about 0.1 and about 5 weight percent of the composite solid.

The liquid phase reaction is performed in aqueous acids having pH values from 0 to about 5. Suitable acids include strong mineral acids whose anions do not precipitate the platinum group or cupric ions. Examples are sulfuric, nitric and hydrohalic acids, particularly hydrochloric and hydrobromic acid. Also useful are the water soluble carboxylic acids which have from 1 to about 5 carbons, e.g., acetic, propionic, isobutyric, valeric, etc. Strongly acid conditions are preferred, having a range of pH values from about 0.5 to about 3. These strongly acid conditions are most favorable because they provide a maximum rate of carbonyl formation, e.g., maximum rate of acetaldehyde synthesis from ethylene. These strongly acid conditions, however, also are the most conducive to oxalic acid formation. Accordingly, our invention shows its maximum utility when applied to the strongly acid system.

The vapor phase reaction is performed in the presence of water vapor and the strong acid which is either impregnated on the catalyst support or introduced as a gas into the reaction zone. A typical vapor feed, on an oxygen free basis, would comprise from 50 to 95 volume percent of the olefin, from 5 to 50 volume percent water vapor and from 0.05 to 5 volume percent of an acidic gas such as hydrogen chloride or hydrogen bromide. In the single stage processing, the proper quantities of oxygen hereafter defined would, of course, be admixed with this mixture.

Because the acidity and the halogen content of the reacting system can change during the reaction, it is preferred to continuously or periodically analyze the catalyst, i.e., either the liquid system or the solid catalyst composite for the necessary content of halogen and to continuously add in response thereto the necessary amounts of any of the aforementioned halogen compounds and/or strong mineral acids such as hydrochloric, sulfuric, nitric, etc. to the system so as to restore the halide and pH conditions respectively.

The maximum activity of the catalyst is achieved by the use of halide ions, particularly chloride or bromide, in the catalyst. Of these, chloride compounds are preferred and in general between about 1 and about 10 weight percent of the catalyst solution or catalyst solid composite should comprise the halogen. In the liquid phase system, the hydrogen halide and/or various halogen salts can be incorporated to supply the requisite amount of halogen. Included in such suitable materials are of course hydrogen chloride and hydrogen bromide which also serve to control the pH as previously mentioned; the alkali metal salts such as sodium chloride, lithium bromide, cesium chloride, as well as the alkaline earth halides such as calcium chloride, magnesium bromide, etc. The same halogen salts can be used to impregnate the solid catalyst used in the vapor phase process. Excess halide will also tend to reduce the catalyst activity and therefore the aforementioned halide concentration should be further limited by the cupric ion concentration so that the ratio of halide to cupric ions is from 1:1 to about 4:1.

The continuous embodiment of the process wherein oxygen and the olefin are concurrently introduced into contact with the catalyst can be achieved by introducing the olefin and oxygen in amounts sufficient to preclude the formation of explosive gas mixtures. To prevent such explosion, it is preferred to employ an oxygen deficient system, i.e., to control the relative rates of introduction of the oxygen-containing gas and the olefin so as to maintain a gas mixture having less than about 15 and preferably less than 3 to 5 volume percent oxygen. When a separate regeneration step is employed, this limitation of course is not applicable and the catalyst regeneration can be performed with relatively pure oxygen or, preferably, with air.

As previously mentioned, when performing the separate regeneration in a liquid phase system, the method can be practiced by circulating the catalyst solution through an olefin oxidation reactor and thereafter passing the reduced solution through an oxidizing zone wherein it is contacted with molecular oxygen, preferably air. The gas phases are withdrawn as separate streams from the olefin oxidation reactor and from the catalyst regeneration zone. The gases withdrawn from the olefin oxidation zone which contain the valuable oxidation products and unreacted olefin and partially condensed and the desired acetaldehyde product separated from the condensate by conventional distillation. Because the reaction provides an almost complete conversion per pass of the olefin, the residue gases recovered from the reactor are relatively free of olefin and need not be recycled. However, when lower conversions are experienced, it is of course feasible to recycle the residual gases from the product recovery step to the olefin oxidation zone for complete conversion of the olefin to the desired carbonyl compound. Because the gas streams from the regeneration and reaction stages are separately treated, air can be used in the reoxidation step and the gases removed therefrom exhausted to the atmosphere.

When a solid bed catalyst is employed, the separate regeneration can be conveniently practiced by interrupting the olefin introduction to the reactor and thereupon introducing the oxygen or oxygen-containing gas for regeneration. At this time, the necessary pH conditions and halogen content of the solid composite can be restored, preferably by introducing a hydrogen halide concurrently with the oxygen-containing gas, e.g., a mixture of hydrogen chloride and oxygen or a mixture of any of the aforementioned hydrogen halides with air.

As previously mentioned, the vapor phase contacting is performed by supporting or distending the catalyst and redox components with a suitable halogen compound when necessary on an inert support. Various inert supports can be employed including, e.g., silicious solids such as silica gel, aluminum silicates, etc.; as well as other inerts such as pumica, titania, alumina, carbon, etc. Also distended on said carrier is a necessary amount of the aforementioned vanadium compounds so as to provide for the continuous destructive oxidation of the oxalic acid byproducts.

Our invention will now be described by reference to the following examples:

EXAMPLE 1

A catalyst solution containing 1 gram of palladium chloride, 2 milliliters of concentrated hydrochloric acid (37% strength), 5 grams of cuprous chloride, and 11 grams of lithium chloride in 500 milliliters of water were introduced into a ½ gallon autoclave. The autoclave was closed and pressured to 500 psig with ethylene and then heated to 250°F. Oxygen was then slowly admitted into contact with the liquid reactants in increments indicated by a rise of 10 psig on a pressure indicator. The pressure was maintained at 600 psig by alternate additions of oxygen and ethylene throughout a 30-minute reaction period. Upon completion of the 30-minute reaction period, the autoclave was cooled, opened and the contents weighed to observe a total weight increase of 148 grams. The product was analyzed to consist essentially of acetaldehyde and acetic acid.

The above reaction was repeated, however, 7 grams of oxalic acid was added to the reactants. No appreciable absorption of oxygen was observed during this experiment, indicating that the oxalic acid effectively inhibited the oxidation.

The above experiment was repeated, however, 7 grams of oxalic acid and 1 gram of vanadyl chloride were added to the autoclave. The oxidation commenced immediately upon the addition of oxygen and after a 30-minute reaction period of total of 184 grams of oxidized product were obtained.

The reaction was repeated with vanadyl sulfate in lieu of the vanadyl chloride of the previous run. Again, instantaneous reactivity of the solution was observed and a total of 135 grams oxidized product were obtained in 30 minutes.

The reaction was repeated; however, the cuprous chloride and oxalic acid were omitted from the reaction zone. A slight activity of the system was observed and a total of 81 grams oxidized product was obtained after a 30-minute reaction period.

The preceding run was again repeated; however, vanadyl sulfate was substituted for the vanadyl chloride previously employed. Again, a slight activity was observed, however, only 59 grams of oxidized product were obtained upon the completion of a 30-minute reaction period.

The preceding examples demonstrate that the presence of a suitable vanadium compound in the aforedescribed oxidation process effectively prevents the inhibition of catalytic activity by oxalic acid. The experiments also demonstrate that a combination of copper and a suitable vanadium compound produces substantially greater yields of oxidized product than are obtainable in the absence of either one of these redox agents.

EXAMPLE 2

The formation of oxalic acid during the oxidation of an olefin was demonstrated by a series of experiments wherein the reaction medium was used repeatedly. The reaction medium initially charged to the autoclave was:

| | |
|---|---|
| Water | 500 grams |
| Palladous chloride | 1 gram |
| Cupric chloride | 5 grams |
| Hydrochloric acid | 3 milliliters (37% HCl) |

The autoclave was closed, pressured to 500 psig with ethylene, then to 900 psig with nitrogen. The reactants were heated to 250°F. and maintained at that temperature while oxygen was introduced at 20 psi increments over a 10-minute period. The autoclave was cooled, opened and the liquid contents removed and distilled to recover 26 grams of product, chiefly acetaldehyde, and a liquid residue which was returned to the autoclave and the procedure repeated. The following yields were obtained:

| Run | Number of Recycles | Distillate Product Total Weight | Acetaldehyde |
|---|---|---|---|
| 1 | 0 | 26 grams | 21 grams |
| 2 | 1 | 29 | 28 |
| 3 | 2 | 30 | 25.3 |
| 4 | 3 | 32 | 17.7 |
| 5 | 4 | 32 | 19.8 |
| 6 | 5 | 28 | 19.5 |

Upon completion of the fifth recycle, the liquid residue was filtered to recover a solid which was washed with water and acetone and dried. The solid was analyzed by infrared to detect a large concentration of cupric oxalate.

The preceding series of experiments was also performed with one gram of ammonium vanadate initially charged to the autoclave. The reaction medium was similarly used throughout the series of six repeated oxidations. Upon completion of the sixth oxidation, the liquid medium was filtered and the solid separated was washed with water and alcohol and dried. Analysis revealed that no oxalate salts were present.

EXAMPLE 3

The process of our invention was studied in a reaction system that permitted continuous processing. Ethylene and oxygen were separately introduced into a titanium reactor of 2½ inches internal diameter. The rate of oxygen introduction was controlled in response to the oxygen content in the reactor effluent gases, the control instrument being set to maintain the oxygen content in these gases less than about 1.0 volume percent. Ethylene was supplied in a large excess to sweep the acetaldehyde product from the reactor and the excess ethylene was separated in the product recovery zone, compressed and returned for further reaction. The liquid contents of the reactor were periodically analyzed and hydrochloric acid was introduced when necessary to maintain a constant halide concentration. The vapor effluent from the reactor was condensed and distilled to recover the acetaldehyde product.

The reactor was charged with the following reaction medium:

| | |
|---|---|
| Water | 700 grams |
| Acetic acid | 300 |
| Palladous chloride | 1 |
| Cupric acetate | 20 |
| Lithium chloride | 5 |
| Lithium acetate | 10 |

Oxygen was introduced at a rate of 50 liters per hour and ethylene at 2,000 liters per hour. The reaction was continued for 6 to 7 hours at 300°F. and 500 psig while hydrochloric acid was added periodically to maintain activity of the catalyst. At the start of each test, 2.5 grams oxalic acid were added to the reaction medium and 1.0 gram of the metal compound indicated in the following table was also added. The following table summarizes the results:

| Test No. | Additional Metal Salt | Cupric Oxalate Present After | |
|---|---|---|---|
| | | 1 Hour | 6 Hours |
| 2 | None | Yes | Yes |
| 3 | NH$_4$VO$_3$ | Yes | No |
| 4 | Cr(OCOCH$_3$)$_2$ | Yes | Yes |
| 5 | SnCl$_2$.2H$_2$O | Yes | Yes (7 hours) |
| 6 | FeCl$_3$ | Yes | Yes (7 hours) |

The data evidence that the presence of a vanadium compound not only prevented the accumulation of cupric oxalate but also destroyed the 2.5 grams of oxalic acid initially charged to the reaction medium. Salts of other metals such as chromic, stannic and ferric salts failed to destroy the oxalic acid during the ethylene oxidation.

The preceding examples are intended solely to illustrate a mode of practicing our invention and to demonstrate the results obtainable thereby. It is not intended that these examples be construed as unduly limiting of the invention which is defined by the method steps and their obvious equivalents set forth in the following claims.

We claim:

1. A process for the selective oxidation of oxalic acid in the presence of acetaldehyde that comprises contacting a liquid phase comprising water, acetaldehyde, a strong mineral acid and oxalic acid with oxygen and catalytic amounts of a vanadium compound soluble in said liquid phase at a temperature of 30° to 300°C. and a pH of about 0.5 to 3.

2. The process of claim 1 wherein said liquid phase contains from 0.01 to 1.0 weight percent of said vanadium compound and a cupric salt soluble in said liquid phase.

3. The process of claim 1 wherein said vanadium compound is a vanadyl salt.

4. The process of claim 1 wherein said vanadium compound is ammonium vanadate.

5. The process of claim 1 wherein said vanadium compound is vanadyl chloride.

* * * * *